(12) United States Patent
Meyers et al.

(10) Patent No.: US 8,743,368 B2
(45) Date of Patent: Jun. 3, 2014

(54) OPTICAL SENSOR SYSTEM AND METHOD OF SENSING

(75) Inventors: Mark Marshall Meyers, Mechanicville, NY (US); Bengt Arne Ivarsson, Balinge (SE)

(73) Assignee: General Electric Company, Niskayuna, NY (US)

( * ) Notice: Subject to any disclaimer, the term of this patent is extended or adjusted under 35 U.S.C. 154(b) by 310 days.

(21) Appl. No.: 12/617,081

(22) Filed: Nov. 12, 2009

(65) Prior Publication Data

US 2011/0109907 A1    May 12, 2011

(51) Int. Cl.
*G01N 21/55* (2006.01)

(52) U.S. Cl.
USPC .......................................................... 356/445

(58) Field of Classification Search
USPC .................................................. 356/445–448
See application file for complete search history.

(56) References Cited

U.S. PATENT DOCUMENTS

| | | | |
|---|---|---|---|
| 5,164,589 A | 11/1992 | Sjodin | |
| 5,313,264 A | 5/1994 | Ivarsson et al. | |
| 5,316,983 A | 5/1994 | Fujimori et al. | |
| 6,466,315 B1 | 10/2002 | Karpol et al. | |
| 6,654,183 B2 * | 11/2003 | Coufal et al. | 359/717 |
| 7,317,519 B2 | 1/2008 | Van Wiggeren et al. | |
| 7,339,681 B2 | 3/2008 | Su et al. | |
| 7,515,270 B2 | 4/2009 | Ogura et al. | |
| 2002/0109846 A1 | 8/2002 | Naya | |
| 2004/0223159 A1 | 11/2004 | Iwata et al. | |
| 2007/0031154 A1 | 2/2007 | Van Wiggeren et al. | |
| 2007/0165232 A1 * | 7/2007 | Mordau et al. | 356/445 |
| 2009/0262357 A1 | 10/2009 | Hoffmann | |

FOREIGN PATENT DOCUMENTS

| | | |
|---|---|---|
| EP | 1219952 B1 | 10/2004 |
| JP | 2003185568 A | 7/2003 |
| WO | 2007026582 A1 | 3/2007 |
| WO | 2011059383 A1 | 5/2011 |

OTHER PUBLICATIONS

Steven K. Dew and Robert R. Parsons; "Absorbing Filter to Flatten Gaussian Beams"; Applied Optics, vol. 31, Issue 18, doi:10.1364/AO.31.003416; Abstract 2pages, 1992.

Jiri Homola and Marek Piliarik; "Surface Plasmon Resonance (SPR) Sensors"; Springer Ser Chem Sens Biosens(2006) 45-67;DOI 10.1007/5346_014; Published online:Jul. 8, 2006.

PCT/SE2010/051233 Written Opinion of International Application Number. Feb. 17, 2011.

WP2007026582 A1 translation from Thompson Scientific Feb. 22, 2011.

* cited by examiner

*Primary Examiner* — Tara S Pajoohi Gomez
(74) *Attorney, Agent, or Firm* — Jenifer E. Haeckl (57) ABSTRACT

An optical detection system is provided for generating and detecting a beam of electromagnetic radiation having intensity. The optical detection system comprises a source for producing the beam of electromagnetic radiation; and a body, that is at least partially transparent and comprises an ATR-sensor layer on at least a portion of the body, having an entrance surface for the beam of electromagnetic radiation, an internally or externally reflective surface that reflects the beam transmitted through the entrance surface, and an exit surface through which the beam, reflected from the second surface, exits the transparent body. The optical detection system may further comprise a distribution device between the beam source and the body; wherein the distribution device redistributes the intensity of the beam from a non-uniform intensity distribution to a substantially uniform intensity distribution; and a detector that detects the beam of electromagnetic radiation exiting the body.

17 Claims, 4 Drawing Sheets

OPTICAL SENSOR SYSTEM AND METHOD OF SENSING

BACKGROUND

The invention relates to an optical sensor system based on attenuated total reflection (ATR), and more particularly to a surface plasmon resonance based optical sensor system and a method for sensing.

Surface plasmon resonance (SPR) based sensors are commercially available for use in research and development. For example, SPR sensors are available from the BIACORE® instrument line from GE Healthcare, Uppsala, Sweden. These commercially available instruments use a sensor glass chip covered with a thin gold film carrying an immobilized chemical sensor layer, and an integrated fluid cartridge for passing sample fluid and other fluids over the sensor chip. A wedge shaped beam of light is coupled to the sensor chip via a prism and a reusable optical interface, such that an angular range of incident light is reflected internally along a line at the glass/gold film interface thus creating a total internal reflection (TIR)-evanescent field at the glass/gold interface. At a unique narrow range of angles for a particular wavelength, this TIR-evanescent field transfers energy from incident light rays through the gold film and creates a surface plasmon wave resonance at the gold film/sensor layer interface. The surface plasmon wave generates an enhanced evanescent electric field that has a characteristic penetration depth into the sample side of the gold surface whereby the refractive index of the sample determines the SPR-angle. A photodetector 2D-array detects the reflected light intensity distribution versus angle of incidence for a row of sensor spots along the illuminated line to produce simultaneously a SPR spectrum for each sensor spot. Upon imaging these multi SPR spectra onto the photodetector the image has bright and dark bands. The sensor measures the angular location of a dark band on the detector surface generated by the resonant coupling of the reflected light and going into the gold film as surface plasmon energy. The angular location of the surface plasmon resonance depends on the refractive index of the sample being penetrated by the SPR evanescent field. The amount of reflected energy will also depend on the degree of absorption of evanescent field energy, as is the case for a sample having a complex valued refractive index at the chosen wavelength.

High sensitivity and high resolution of SPR-spectroscopy is desirable, particularly in the case of kinetic studies. Also in the field of high-throughput biomolecular screening, high sensitivity is desirable for SPR-spectroscopic and other ATR-spectroscopic methods.

The sensitivity or resolution in the detectable change of the angle (or wavelength) at the dip or peak (or in some cases, dips or peaks), or centroid (center-of-mass) of the SPR reflection curve is mainly limited by the degree of constancy, drift and noise of the background light intensity of the total internal reflection curve (TIR-curve). Ideally, the TIR-curve is constant with respect to the angle of incidence. In practice, however, due to variation of reflectance with the angle of incidence, and due to the radiation distribution from the light source, the emitted light beam cross intensity profile, and as a consequence also the TIR-curve is generally a Gaussian type curve with at least one maximum. The reflectance may vary due to several reasons, such as, reflection losses in the coupling of light between prism (or grating) and the plasmon supporting metal. A constant background intensity pattern can be normalized by a suitable software algorithm. However, a changed background image and/or too large correction will introduce a "normalization error". Irrespective of the type of algorithm used for calculation of the dip, peak, centroid (center-of-mass), etc. ATR-spectrum curvature characteristics, this "normalization error" must be minimized in a high resolution ATR-sensor instrument. Using normalization over a large variation in intensity across the detector array leads to a decreased signal to noise ratio in the lower intensity areas on the edge of the detector array. Generally, the differences between detected Gaussian-type light source intensity distributions and mathematically created, and measured normalized intensity distributions are too large.

For high sensitivity or high resolution of ATR-sensor devices, and in particular SPR-sensors, it is desirable that some area of interest on the sensor surface be illuminated as uniformly as possible, providing a TIR-curve with flat-top intensity profile.

A conventional surface plasmon resonance (SPR) measurement system typically comprises one or more light emitting diodes (LEDs) that at TIR illuminate the surface plasmon sensor device. LEDs have a coherence length that is long enough to enable an SPR measurement system to detect small shifts in SPR resonances. The ability to detect small shifts in SPR resonances enables the system to be highly accurate and highly sensitive or to otherwise improve the resolution.

Typically, light from an LED is Lambertian (diffuse light emitted into a hemisphere with a cosine drop off in intensity) and has low optical power. These properties of the LED can reduce the amount of light that is incident on an ATR-sensor device and decrease the signal-to-noise (SNR) ratio, which can correspondingly reduce the accuracy and sensitivity or resolution of the SPR measurement system. The required high optical power incident on the ATR-sensor may be delivered using edge-emitting light sources, like edge-emitting diodes, superluminescent diodes, and laser diodes, due to their highly directional beam of high intensity in a narrow radiation angle.

High power solid-state light sources, like edge-emitting diodes, superluminescent diodes, and laser diodes, produce a highly directional beam of light. Also, when these light sources are coupled to optical waveguides or fibers, the output optical beam from the waveguide or fiber is also highly directional. However, most of the high power sources have an extremely inhomogeneous light intensity. Specifically, the light intensity of a high power beam follows a Gaussian distribution. The non-uniform or Gaussian type intensity distribution of the beam incident onto the detector limits the sensitivity and resolution of the ATR-spectrometer when these light sources are either directly used in SPR-sensing, or are followed by a focusing optics.

The optical power inhomogeneity limits ATR-sensors, because the resolution is too low for biological interaction. For example, simultaneous high resolution and accurate detection of multi spot arrays is necessary in the field of high-throughput screening for pharmaceutical development. Therefore, there is a need for a high power (directional) beam that has a uniform optical intensity.

BRIEF DESCRIPTION

In one embodiment, an optical detection system of the invention, for generating and detecting a beam of electromagnetic radiation having intensity, comprises a source for producing the beam of electromagnetic radiation; and a body, that is at least partially transparent and comprises an ATR-sensor layer on at least a portion of the body, having an entrance surface for the beam of electromagnetic radiation, an internally or externally reflective surface that reflects the beam transmitted through the entrance surface, and an exit surface through which the beam, reflected from the second surface, exits the transparent body. The optical detection system may further comprise a distribution device between the beam source and the body; wherein the distribution device redistributes the intensity of the beam from a non-uniform intensity distribution to a substantially uniform intensity distribution; and a detector that detects the beam of electromagnetic radiation exiting the body.

Another embodiment of the system of the invention, can be used as an optical subsystem for use in an SPR detection system, and comprises, an electromagnetic radiation source adapted to produce a beam having an intensity distribution on a single plane, a fluidic flow cell, and an SPR detector associated with the fluidic flow cell. The optical subsystem comprises a lens that collimates the beam, an aspherical lens that modifies the beam so that the intensity of the beam has a flat top distribution, a second aspherical lens that collimates the modified beam, and a cylindrical lens that converts the collimated modified beam to an anamorphic beam and focuses the beam on a interface of a plasmon generating metal film and the fluidic flow cell via a prism.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The invention relates to the optical detection systems for generating and detecting the beam of electromagnetic radiation. In one of the embodiments, the optical detection system comprises a source for producing the beam of electromagnetic radiation, and a body that is at least partially transparent. An ATR-sensor layer is disposed on at least a portion of the body. The body has an entrance surface for the beam of electromagnetic radiation, an internally reflective surface that reflects the beam transmitted through the entrance surface, and an exit surface through which the beam reflected from the second surface exits the transparent body. The body may be fully transparent at least partially transparent to the light from the optical source. For example, the body is fully transparent. The body may be a prism. The optical detection system further comprises a distribution device disposed between the beam source and the body, wherein the distribution device redistributes the intensity of the beam from a non-uniform intensity distribution to a substantially uniform intensity distribution. The optical detection system further comprises a detector that detects the beam of electromagnetic radiation exiting the body. The optical detection system is also referred to herein as an SPR system.

As used herein, the term "electromagnetic radiation" means radiation in the ultra-violet region (from about 10 nm to about 400 nm), visible region (from about 400 nm to about 750 nm), and in the infrared region (from about 750 nm to about 20μ·m), i.e. in the wavelength range from about 0.4.μ·m to about 20.μ·m. For simplicity, it will be also referred to as "light".

In certain embodiments the wavelength range in a range from about 600 nm to about 900 nm. In one embodiment, the electromagnetic radiation has a wavelength of about 785 nm. The broad range of wavelengths enable imaging across a broad range of biologically relevant wavelengths and allow surface plasmon evanescent waves to penetrate into the biological sample. The electromagnetic radiation source comprises at least one of, an edge-emitting diode, a superluminescent diode, or a laser source. The electromagnetic radiation source may in alternative embodiments be connected to an optical fiber, where the fiber output end is adapted to produce the beam having a nonuniform intensity distribution.

The edge-emitting light source or a fiber coupled light source with a small emitting area generally causes a focal line width that is too small, which, in combination with anamorphic imaging, due to optical imperfections, results in a speckled ATR-image. Thus, it is desirable to use a surface emitting diode that has a larger emitting area or to magnify the emitting area of the edge-emitting diode, by use of a lens or lens system enclosing spherical and/or aspherical surfaces. In one embodiment, the anamorphic beam is a wedge shaped beam.

In one embodiment, the ATR-sensor layer comprises a plasmon generating metal film. The ATR-sensor layer is an evanescent wave generating layer. The plasmon generating film, typically a free-electron like metal, comprises metal compounds, metal film layer structure, metal layer surface texture, or a suitably doped semiconductor film. The plasmon generating metal film comprises one or more of, gold, silver or any other plasmon generating metal or mixtures or alloys thereof. The ATR-sensor layer is disposed on the transparent body and is positioned close enough to the incident light to enable plasmon generation in the metal film. The internal reflective surface of the body supports the plasmon-generating metal film. The metal film is probed by the evanescent wave elicited by total internal reflection (such as in ATR). The internally reflective surface, along with the metal films, is often referred to herein as a sensor surface. In one embodiment, the distance between the metal film and the incident light is such that the evanescent waves can interact with the plasma electrons in the surface and excite the plasmons. The light incident on the bottom of the prism is probing the sample through the plasmon wave evanescent field.

One or more immobilizing layers may be disposed on the plasmon generating metal film surface. The immobilizing layer helps to immobilize the interacting moiety on the sensor surface. The presence of the interacting moiety on the plasmon generating metal film facilitates a change in a parameter of the environment of the sensor surface. For example, the presence of interacting moiety may cause the change in the refractive index of the environment of the sensor surface. When the light beam falls onto the metal film at a specific (resonance) angle, the metal surface electrons are set to resonate with the light exciting the plasmons. The resonance results in the absorption of light and hence the dip in the ATR-spectrum intensity curve. For the purpose of this description, the portion of the body having the ATR-sensor layer comprising the plasmon generating film and/or one or more immobilizing layers may also be referred to as a sensor surface.

There are two common ways of coupling the light to a sensor surface for creating an evanescent wave, by a prism or a grating. In the prism-coupling case, the sensor surface may be a surface of the prism or that of a separate sensor element, such as a glass or plastic plate, in optical light-coupling contact with the prism, such as via a refractive index matching medium. In the latter example, the "internally reflective surface" will be a surface of this separate sensor element. In the grating-coupling case, the sensor surface may be integral with the grating element (e.g. one face of a glass or plastic plate with the grating formed on the opposite face, or it is actually a part of the grating). As in the prism case, the sensor element may also be a separate element in optical contact with a grating element.

The source for producing the beam of electromagnetic radiation is also referred to as "light source". The light source can be selected from a natural source, direct chemical source, combustion based source, electric powered source, lasers, laser diodes, or super-luminescent diodes (SLED). In one embodiment, the source is a solid state light source, for example, light emitting diodes (LED) in the shape of a surface emitting diode or an edge-emitting diode, a super-luminescent diode (SLED) or a laser diode. Due to the solid state photon emitting properties of the source, the intensity variation across the focal line illumination (also referred to as beam shape or beam profile) is a Gaussian profile. The source for producing the beam of electromagnetic radiation may, in some embodiments, be referred to as a Gaussian source. The terms "light source" and "Gaussian source" may be used herein interchangeably. In one embodiment, the light source may be a high-energy source. In this embodiment, the energy source may have, for one photon of light, a wavelength between 600 and 900 nm. Advantageously, the high power light source has high directional properties. A directional light source has parallel light rays that travel in one direction along the specified vector. Directional light may contribute to diffuse and specular reflections, which in turn depend on the orientation of an object's surface but not its position. A directional light may not contribute to ambient reflections. The high directional properties of high power light source enable a higher intensity of light to be incident on the target, thereby increasing the signal-to-noise (SNR) ratio. A high SNR increases the accuracy and sensitivity of the SPR measurement system.

The non-uniformly distributed intensity light, if used, could result in difficulty in correlating the dip in the ATR-spectrum intensity profile. If a Gaussian profile intensity light beam is used for the detection purpose, then the dip in the intensity profile of the reflected beam will be somewhere within the Gaussian profile. Due to the dip in the intensity profile of the reflected beam, a dark SPR attenuation band forms when the reflected beam falls on the detector. The accuracy of the location of the dark band on the detector surface will depend on which row of the detector the dark band occurs on. If the band occurs on the bright peak of the intensity distribution the signal will be high, and the SNR will also be high, but if the dark band occurs on the dimmer edges, the SNR will be low. The system of the invention allows the SNR to be high over the full range of measurement.

The high power source in the optical detection system may comprise a super-luminescent diode (SLED), laser diode, a solid-state laser, a gas laser, a semiconductor laser with an external cavity, or any other type of laser with sufficiently high power and a sufficient amount of directional light to illuminate the target and provide a suitable SNR for the optical detection system.

The invention allows the use of high power Gaussian sources in applications that require uniform intensity distributions at the sensor plane. In certain embodiments, laser and fiber coupled sources may be employed as illumination inputs in SPR refractive index measurements. For example, laser and fiber coupled sources used in protein concentration analysis apparatus may be employed without causing a variation in signal to noise performance across the field of view (the angular extent of a given scene that is imaged) of the sensor. The Gaussian source may be, but is not necessarily limited to, an edge emitting laser diode, a gas laser, a solid-state laser, or a light source coupled to a fiber optic cable.

An embodiment of the optical detection system of the invention comprises an ATR-sensor enables the simultaneous detection of a plurality of specific interactions with improved angular or wavelength resolution. The system may also be adapted for detection techniques based on cylindrically focused ATR-reflection, multiple angle critical angle reflectometry, internal multiple-angle Brewster angle reflectometry, multiple-angle evanescent ellipsometry, and variable angle total internal reflection fluorescence.

Performance of the SPR system is dependent on the signal to noise ratio achieved on the detector array. The system noise level is proportional to the square root of the intensity of the illumination projected onto the sample. The system allows for intensity increase of the light incident on the sample of 10 to 100 folds than that achieved with LED or filament lamp sources without requiring significant increase in electrical power consumed by the unit or causing problematic variations in signal to noise (SNR) across the sample. The system also allows the SNR to be maintained over the whole area of the detector array even with high irradiance laser and fiber coupled sources.

In certain embodiments, the intensity profile of the incident electromagnetic radiation may be altered to provide a profile that has substantially uniform intensity distribution. As used herein, the term "substantially" is defined as falling within industry recognized manufacturing tolerances, and ordinary and anticipated dimensional variations in the process and may encompass variations in a range from about −5 percent to about +5 percent. The substantially uniform distribution of the intensity profile prevents the formation of dip/peak in the middle portion of the Gaussian intensity distribution. In certain embodiments, the light beam from the source is made incident on the distribution device before being incident on the sample. The distribution device comprises one or more aspherical lenses. The aspherical lens or lenses form the intensity, or optical power, preserving, aspheric beam-shaping optics of the system. The distribution device preserves the optical power to a much higher degree and simultaneously levels out a non-uniform intensity profile. The distribution device may comprise at least a pair of aspherical lenses also referred to as the aspherical beam intensity converting lenses. The aspherical beam intensity converting lenses comprise at least a pair of different lenses. One of the lenses is concave in shape (concave aspherical lens) that redistributes the high intensity centre portion of the light beam towards the edges of the beam. The other lens is convex in shape (convex aspherical lens) that converge the light beam in a uniform intensity distributed light beam.

The distribution device may be disposed between the beam source and the body or sensor surface. The position of the disposed part of the distribution device between the beam source and the body or sensor surface may depend upon the Gaussian intensity profile of the light source. The optical system may further comprise a first collimator between the beam source and the distribution device and a second collimator between the distribution device and the body.

The aspheric lenses have an image plane diameter from about 10 mm to about 20 mm The aspheric lenses may be made by using the Zemax aspherical sign convention and by removing the volume. Aspheric lenses may comprise, but are not necessarily limited to, any moldable or ground and polished transparent material such as optical plastic (for example, polystyrene, acrylic, cyclic olefin copolymer (COC), polycarbonate) or glass.

In another embodiment, the optical detection system further comprises a magnifying lens subsystem for magnification of emitting area of the electromagnetic radiation. The magnifying lens subsystem comprises a spherical lens, aspherical lens, anamorphic lens, bifocal lens or combinations thereof. The magnifying lens subsystem is used for magnifying an emitting area about 2 to 5× the original size, and for creating a virtual emitting area (real image), the light from which is fed into the distribution device. The magnification feature can be adjustable over the 2 to 5× magnification range.

In one embodiment, the optical sensor system comprises a manual controller, correlated manual controller, automatic optomechanic controller, electro-optomechanic controller, or combinations thereof. The optical sensor system may be programmed to use an actual light intensity distribution for ATR-spectra, in combination with a selected focal line, to manually or automatically control and/or adjust the optomechanics or electro-optomechanics of the system. A controller may also be used to automatically adjust the optical elements of the distribution device, the magnifying lens subsystem or other optical elements in the optical sensor system as needed.

Figure 1:
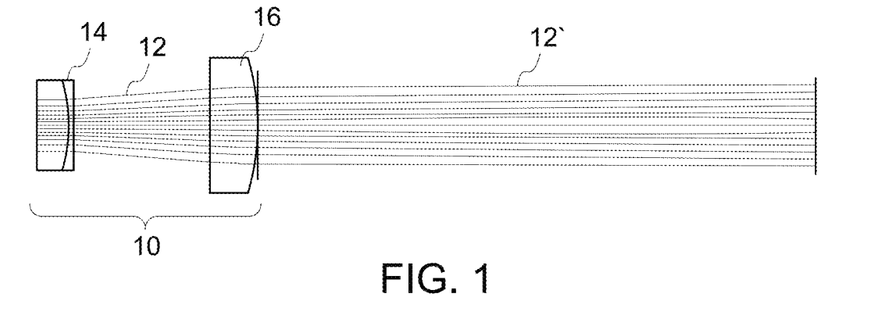
FIG. 1 is a schematic sectional drawing of an example of the distribution device of the invention showing the electromagnetic radiation (light) beam passing through the distribution device.

FIG. 1 illustrates a distribution device 10 having a pair of aspherical lenses (aspherical beam intensity converting lenses) 14 and 16. The pair of aspherical beam intensity converting lenses comprises a first aspheric lens 14 that re-maps the higher intensity areas in the center of the beam (non-uniform intensity distribution beam) 12 radially further out. The radially furthered out beam then falls on the second aspherical lens 16, which then collimates the beam. The collimated beam has a uniform or flat top intensity distribution 12'.

Figure 2:
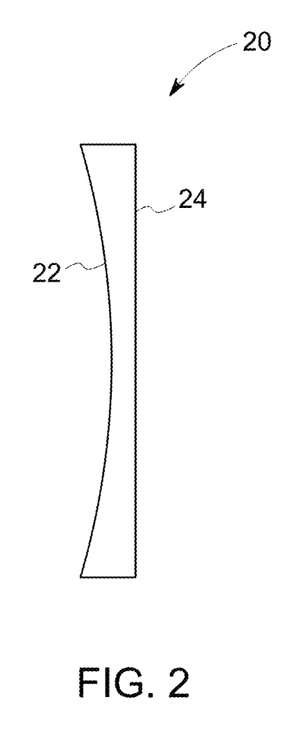
FIG. 2 is a drawing of an example of a concave aspherical lens of the invention.
Figure 3:
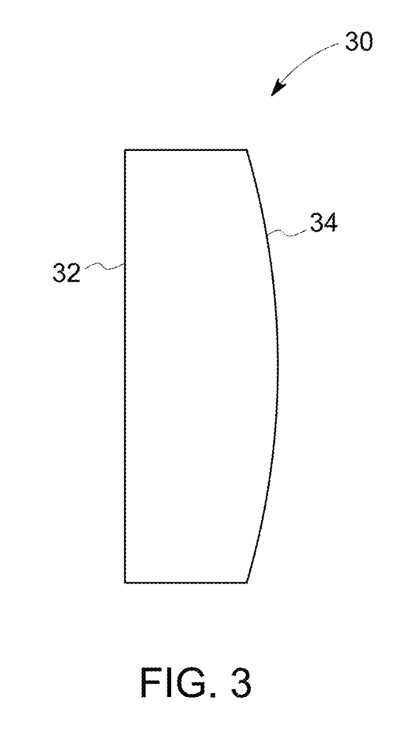
FIG. 3 is a drawing of an example of a convex aspherical lens of the invention.

As illustrated in FIG. 2, the first aspherical lens 20 has a concave surface 22. The light having the non-uniform intensity distribution enters the lens 20 through the surface 22. The light beam exits through a flat surface 24. As illustrated in FIG. 3, the second aspherical lens 30 has a flat surface 32. The light exiting through the flat surface 24 of lens 20 enters the lens 30 through the surface 32. The light beam exits through a convex surface 34. The exited light beam through convex surface 34 has uniform intensity distribution.

Figure 4:
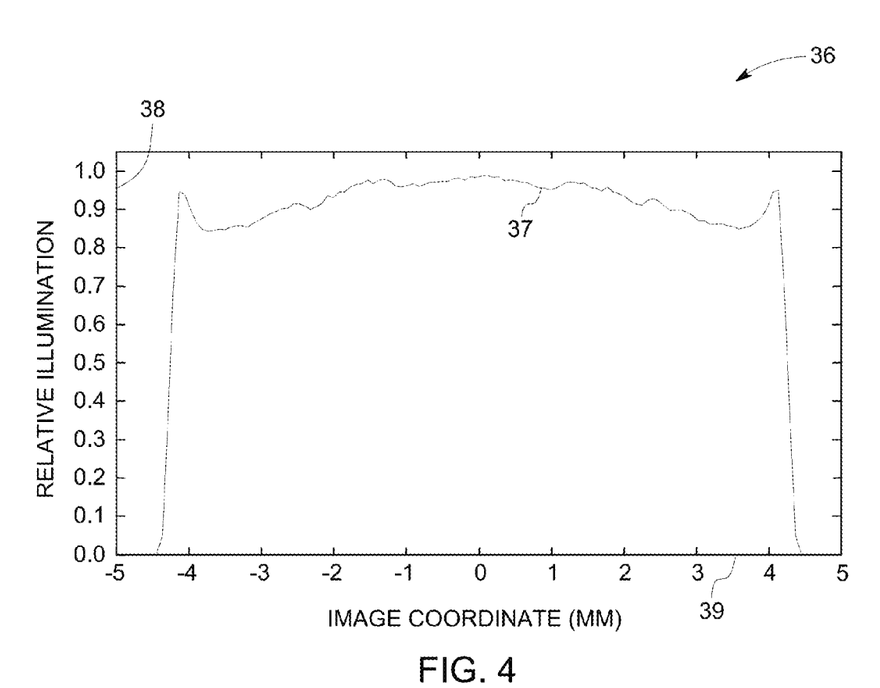
FIG. 4 is a graph showing an example of a flat top intensity distribution.

As illustrated in FIG. 4, the intensity profile 36 of the incident electromagnetic radiation has substantially uniform intensity distribution 37. Ordinate 38 represents intensity, and abscissa 39 represents image co-ordinates.

Figure 5:
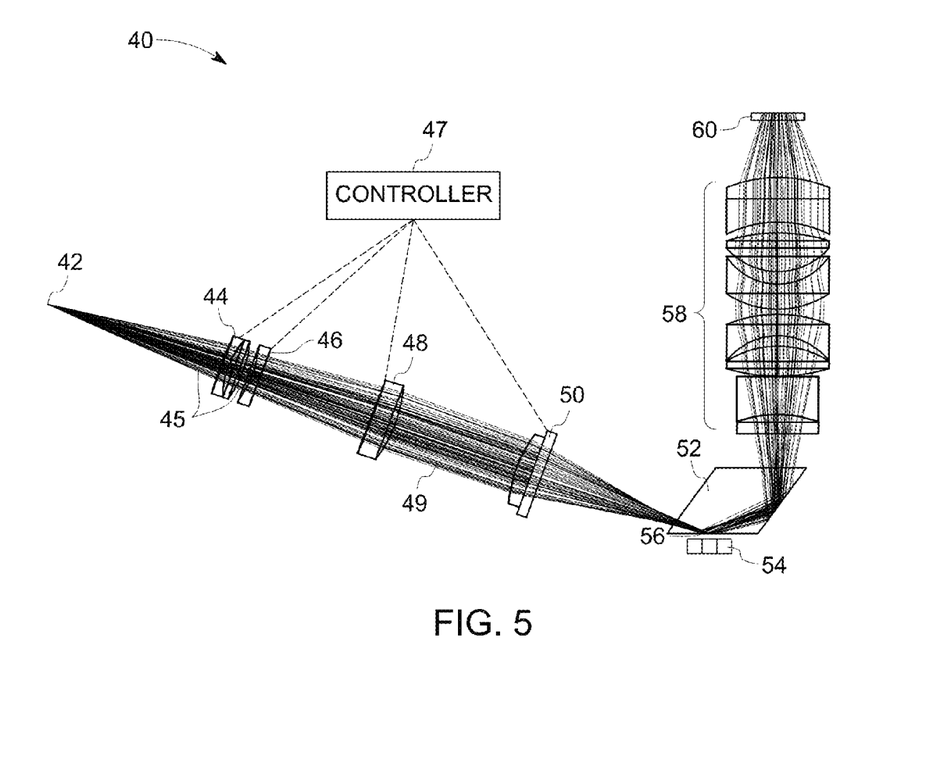
FIG. 5 is a schematic drawing of an example of the optical detection system of the invention.

FIG. 5 illustrates an optical detection system 40 for generating and detecting a beam of electromagnetic radiation having intensity. The system 40 comprises a source 42 for producing the beam of electromagnetic radiation. The system 40 comprises a body 52 that is at least partially transparent. The body 52 comprises a plasmon-generating metal film on at least a portion of the body 52. The body 52 has an entrance surface for the beam of electromagnetic radiation, an internally or externally reflective surface that reflects the beam transmitted through the entrance surface, and an exit surface through which the beam reflected from the second surface exits the transparent body. The optical detection system 40 comprises a distribution device (comprising aspherical lens 46 and second aspherical lens 48) between the beam source 42 and the body 52, wherein the distribution device redistributes the intensity of the beam from a non-uniform intensity distribution 45 to a substantially uniform intensity distribution 49. The power of the uniform intensity distributed light beam (the redistributed beam) 49 has a power in the range of about 85 percent to about 100 percent of the power of the light beam from the source 42. The optical detection system 40 comprises a detector 60 that detects the beam of electromagnetic radiation exiting the body 52 after passing through the anamorphic imaging subsystem 58. The optical detection system 40 comprises a controller 47 that may be connected physically to a first collimator (first beam collimator) 44, aspherical lens 46, second aspherical lens 48, and a cylindrical lens (second beam collimator) 50.

Figure 6:
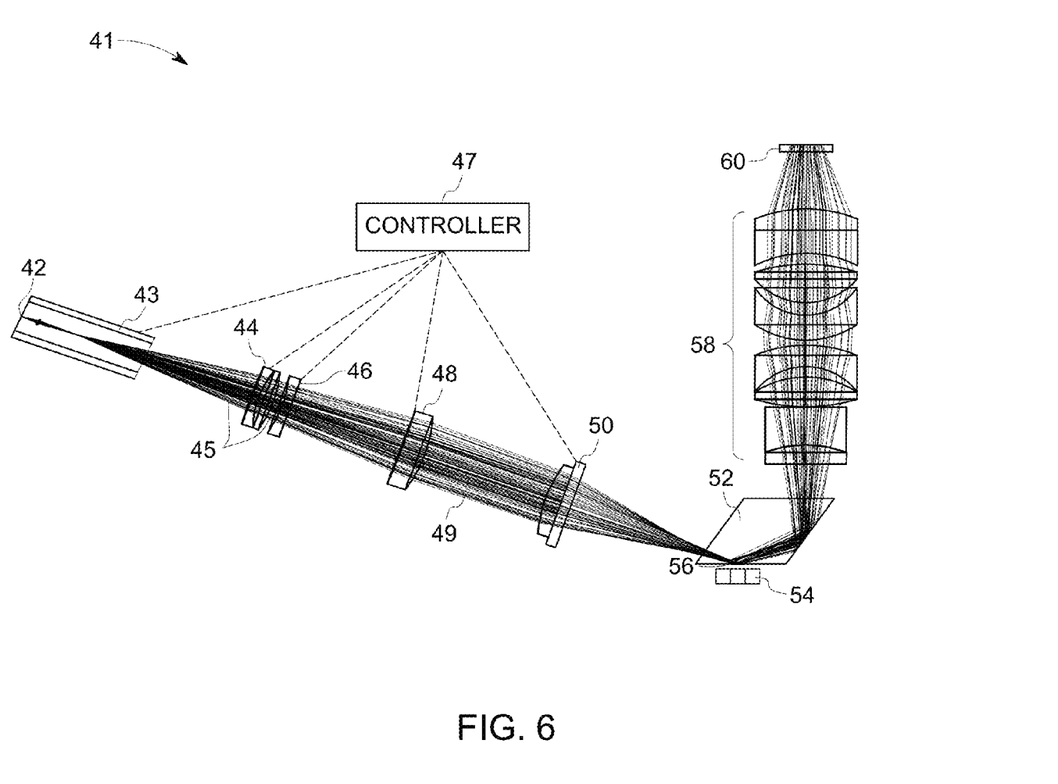
FIG. 6 is a schematic drawing of an example of the optical detection system comprising a magnifying lens subsystem of the invention.

FIG. 6 illustrates an optical detection system 41 for generating and detecting a beam of electromagnetic radiation having intensity. In addition to the components of system 40 disclosed in FIG. 5, the system 41 includes a magnifying lens subsystem 43 between the source 42 and a first beam collimator 44. The magnifying lens subsystem 43 is used for magnifying the emitting area in the range about 2 to 5× magnification, and creating a virtual emitting area (real image), the light from which is fed into the aspherical lens 46 through the first beam collimator 44. The controller 47 of FIG. 6 may further be physically connected to the magnifying lens subsystem 43.

Figure 7:
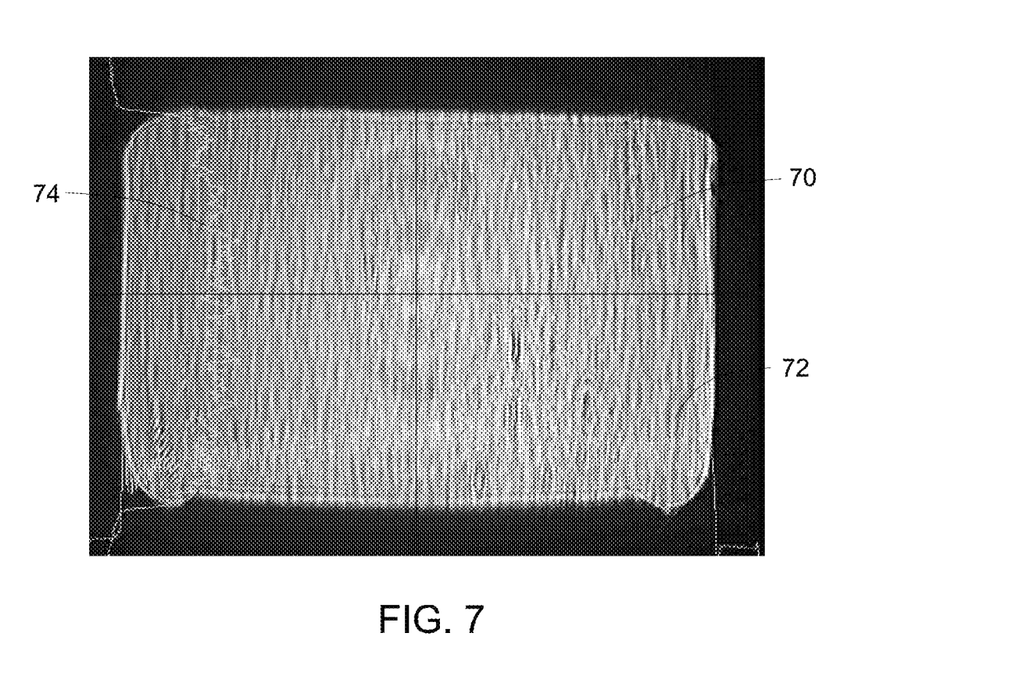
FIG. 7 is a total internal reflection image with a flat top intensity profile.

FIG. 7 illustrates a total internal reflection image (no attenuation caused by surface plasmon resonance, or other light absorption), of which the intensity is uniform or the flattop intensity profiles 70. Curve 72 is the intensity profiles measured in the horizontal (tangential) direction, and curve 74 is the intensity profiles measured in the vertical (sagittal) direction. The system configuration for generating the flattop intensity profile 70 is super luminescent diode/optical fiber/distribution device/ATR-prism/imaging system/image detector.

A flow system 54 is in operative association with the sensor surface 56. The flow system 54 is a microfluidic flow system having a plurality of flow cells. The sample solution flows through the flow cell. The sample solution may have a interacting moiety that may get reversibly or irreversibly immobilized on the sensor surface 56. The immobilizing layer helps immobilize the interacting moiety on the sensor surface 56.

The optical subsystem also comprises the first beam collimator 44 that collimates the beam, an aspherical lens 46 that modifies the beam so that the intensity of the beam has a flat top distribution, a second aspherical lens 48 that collimates the modified beam and a cylindrical lens 50 which is a second beam collimator that converts the collimated modified beam to an anamorphic beam or a wedge shaped beam and focuses the beam onto the dielectrics or the plasmon generating metal film interface at the fluidic flow cell via a body 52. A fluid flow cell may comprise one or more than one fluid flow cell adjacent to the ATR-sensor layer.

Light energy incident at the total internal reflection angles is resonantly absorbed through SPR and removed from the transmitted beam. Light that is not absorbed through the SPR is reflected from the sample and is imaged by an imaging lens system 58 onto the detector 60 arrays. The light from the tangential direction may be Fourier transformed (FT) onto the detector 60 plane. The Fourier transformation may simplify the spatial distribution of the light, for example. A fan-shaped beam (cylindrically focused beam) creates a focal line illumination along one row of sensor spots. The focal line width along the sensor surface determines the length of the sensor spot along which the FT imaging occurs. The light from the sagittal plane is collimated and projected onto the detector 60 array. The detector 60 is an image detector and is positioned at the image focus plane to detect rays lying mainly in the sagittal plane, while being positioned at the back focal plane (or the diffraction plane) to detect rays lying mainly in the tangential plane. This image detector 60 forms a bifocal imaging subsystem.

In anamorphic imaging subsystem, a sensor spot, such as a square, is imaged as a rectangle (band), where the width of the rectangle is the real image of the sagittal width of the sensor spot, whereas the length of the rectangle is a projection of the range of angle of reflectance. The intensity variation along such a rectangular part of the image provides a reflectance curve of the corresponding sensor spot. This enables a simultaneous spatial separation of sensor spot images (real imaging) while monitoring the sample interaction at each individual spot through changes in said reflectance curve. The angular location of the dark band (the dark band appears on the detector sensor which is basically the dip in the intensity curve) provides a very sensitive measure of the concentration of various biomolecules e.g., proteins in the fluid flow cell.

The optical subsystem of this embodiment comprises SPR detector 60 which may be selected from a diode array semiconductor PIN-diode (intrinsic semiconductor region between a p-type semiconductor and an n-type semiconductor-diode) array, a scintillator-based array, a CCD (charge-coupled device detector) array, a TFT- (thin-film transistor) or CMOS- (Complementary metal-oxide-semiconductor detector) based detector, or a PSD (position sensitive device) sensor detector. The optical subsystem also comprises at least one sample flow cell. For a fluidic sample, for example, the fluid flow cell is adjacent to an ATR-sensor layer and a plasmon generating metal film.

One or more of the embodiments of the system of the invention may use the following FT-imaging parameters as described in the following, non-limiting examples:

EXAMPLE 1

For a focal line width in the order of 0.5 mm along the sensor surface, rays of identical angle of reflectance within the illuminated sensor spot create smooth reflectance curves. This focal line width is conventionally provided by a cost-effective design consisting of a conventional surface emitting LED together with a collimator lens (spherical or aspherical) and a cylindrical focusing lens. Typically, the diameter, or side, of the surface-emitting area is 0.2 mm In this case, normal imperfections in high quality optics do not disturb the reflectance curve. Low quality optics and/or low class surface cleanliness may disturb the reflectance curve in the form of more or less shadowed local areas. Due to the high degree of smoothness in these reflectance curves only a (software) normalization of the less pronounced Gaussian shaped total reflectance curve is required. For a surface emitting LED characterized by a non-uniform intensity distribution beam, its combination with the optical detection system 40 will provide the required flat-top profile.

EXAMPLE 2

For a focal line width in the order of 0.1 mm along the sensor surface, rays of identical angle of reflectance within the illuminated sensor spot create a reflectance curve which curvature is often disturbed by sharp peaks and dips (notches). This focal line width is provided by a cost-effective design consisting of a conventional edge-emitting LED, superluminescent diode, or laser diode together with a collimator lens (spherical or aspherical) and a cylindrical focusing lens. Typically, the diameter, or side, of the edge-emitting area is 0.004 mm In this case, normal imperfections in high quality optics do create notches in the reflectance curve. Due to the high degree of notches in these reflectance curves, a suitable (software) curve data smoothing algorithm processing is required before the normalization of the highly pronounced Gaussian shaped total reflectance curve. Aside of the obvious increase in complexity in curve data processing, the price for reducing the notches by smoothing algorithms (ranging from conventional "running average" or "box-car smoothing" to advanced like fast inverse Fourier Filtering) is a more complex interpretation of the monitored changes in the reflectance curve due to changes in opto-mechanical alignment and/or temperature for a practical instrumentation, which often reduce the characteristics in e.g., a SPR-reflectance curve (i.e., the dip in reflectance becomes less pronounced). This "over-smoothing" of the reflectance curve adds a risk of also obtaining a disturbed sensitivity in the detection e.g., the angular shift in the SPR-curve. This drawback is eliminated by the use of the optical detection system 40.

EXAMPLE 3

For a focal line width about 0.4 mm along the sensor surface, rays of identical angle of reflectance within the illuminated sensor spot create a pronounced Gaussian shaped reflectance curve, the curvature of which has a smoothness that is required for most applications. Typically, the diameter, or side, of the edge-emitting area is 0.004 mm This focal line width is achieved by a cost-effective design that comprises a conventional edge-emitting LED, superluminescent diode, or laser diode, together with a magnifying lens or lens subsystem (spherical, aspherical, and bifocalic) which magnifies the edge-emitting area in the range from about 2 to 5× magnification. This creates a virtual edge-emitting area from which the beams are then directed into the first beam collimator lens 44 and a cylindrical focusing lens.

EXAMPLE 4

For a focal line width variable between 0.1 mm to 0.4 mm along the sensor surface, rays of identical angle of reflectance, within the illuminated sensor spot, create a reflectance curve, the curvature of which has a smoothness that is required for most applications. Typically, the diameter, or side, of the edge-emitting area is 0.004 mm This focal line width is achieved by a cost-effective design that comprises a conventional edge-emitting LED, superluminescent diode, or laser diode, together with an adjustable (zoom-able) magnifying lens or lens subsystem (spherical, aspherical, and bifocalic) which may be set manually or automatically (e.g. electronically/digitally) to magnify the edge-emitting area about 2 to 5×. This creates a virtual edge-emitting area of adjustable size from which the beams are directed into the first collimator lens 44 and a cylindrical focusing lens. This embodiment may require a correlated adjustment (zooming) of the optics for the magnification of the light source and the optics for collimation, beam-shaping, and cylindrical focusing.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. An optical detection system for generating and detecting a beam of electromagnetic radiation having an intensity, comprising:
   a source for producing the beam of electromagnetic radiation;
   a body, that is at least partially transparent and comprises an ATR-sensor layer on at least a portion of the body that comprises a plasmon generating film that is adapted to generate an evanescent wave, having an entrance surface for the beam of electromagnetic radiation, a reflective surface that reflects the beam transmitted through the entrance surface, and an exit surface through which the beam reflected from the second surface exits the transparent body;
   a distribution device between the beam source and the body; wherein the distribution device redistributes the intensity of the beam from a nonuniform intensity distribution to a substantially uniform intensity distribution, and generates an intensity profile to produce a signal-to-noise ratio over a full measurement range of the intensity profile; and
   a detector that detects the beam of electromagnetic radiation exiting the body.

2. The optical sensor system of claim 1, wherein the distribution device comprises one or more aspherical lens.

3. The optical sensor system of claim 1, wherein the distribution device comprises a concave aspherical lens and a convex aspherical lens.

4. The optical sensor system of claim 1, further comprising a first beam collimator between the beam source and the distribution device.

5. The optical sensor system of claim 4, further comprising a second beam collimator between the distribution device and the body.

6. The optical system of claim 1, wherein source for producing the beam of electromagnetic radiation comprises at least one of a surface emitting diode, an edge-emitting diode, a superluminescent diode, or a laser source.

7. The optical system of claim 1, wherein the source for producing the beam of electromagnetic radiation is coupled to an optical fiber.

8. The optical sensor system of claim 1, further comprising a controller for the distribution device, that is selected from one or more of a correlated manual controller, an automatic optomechanic controller, or an electro-optomechanic controller.

9. The optical sensor system of claim 1, further comprising a magnifying lens subsystem that magnifies the emitting area of the electromagnetic radiation.

10. The optical sensor system of claim 9, wherein the magnifying lens subsystem comprises a spherical lens, aspherical lens, anamorphic lens, or combinations thereof.

11. The optical sensor system of claim 9, wherein the magnification range of the magnifying subsystem is 2 to 5×.

12. The optical sensor system of claim 9, comprising a manual controller, automatic optomechanic controller, electro-optomechanic controller, or combinations thereof.

13. The optical sensor system of claim 1, wherein the beam comprises high power electromagnetic radiation.

14. The optical sensor system of claim 1, wherein the ATR-sensor layer is adjacent to a fluidic flow cell.

15. The optical sensor system of claim 14, wherein the ATR-sensor layer comprises a plasmon generating metal film comprising gold, silver, or alloys thereof.

16. The optical sensor system of claim 1, wherein the redistributed beam has a power in the range of about 85 percent to 100 percent of the power of the beam from the source.

17. The optical sensor system of claim 1, wherein the substantially uniform intensity distribution has a flat top intensity distribution.

* * * * *